US009505701B2

(12) United States Patent
Garbark et al.

(10) Patent No.: US 9,505,701 B2
(45) Date of Patent: Nov. 29, 2016

(54) METHOD FOR THE PRODUCTION OF ESTERS AND USES THEREOF

(71) Applicant: PETROLIAM NASIONAL BERHAD, Kuala Lumpur (MY)

(72) Inventors: Daniel B. Garbark, Blacklick, OH (US); Herman Paul Benecke, Columbus, OH (US)

(73) Assignee: Petroliam Nasional Berhad, Kuala Lumpur (MY)

( * ) Notice: Subject to any disclaimer, the term of this patent is extended or adjusted under 35 U.S.C. 154(b) by 0 days.

(21) Appl. No.: 14/381,530

(22) PCT Filed: Feb. 28, 2013

(86) PCT No.: PCT/MY2013/000038
§ 371 (c)(1),
(2) Date: Aug. 27, 2014

(87) PCT Pub. No.: WO2013/129907
PCT Pub. Date: Sep. 6, 2013

(65) Prior Publication Data
US 2015/0080599 A1 Mar. 19, 2015

Related U.S. Application Data

(60) Provisional application No. 61/604,267, filed on Feb. 28, 2012.

(51) Int. Cl.
| C07C 67/08 | (2006.01) |
| C07C 67/29 | (2006.01) |
| C07C 67/39 | (2006.01) |
| C07C 69/02 | (2006.01) |
| C07C 69/22 | (2006.01) |
| C07C 69/34 | (2006.01) |
| C07C 69/675 | (2006.01) |
| C11C 3/00 | (2006.01) |
| C11C 3/04 | (2006.01) |

(52) U.S. Cl.
CPC .............. *C07C 67/29* (2013.01); *C07C 67/08* (2013.01); *C07C 67/39* (2013.01); *C07C 69/02* (2013.01); *C07C 69/22* (2013.01); *C07C 69/34* (2013.01); *C07C 69/675* (2013.01); *C11C 3/006* (2013.01); *C11C 3/04* (2013.01)

(58) Field of Classification Search
CPC ....... C07C 67/08; C07C 67/29; C07C 67/39; C07C 69/02; C07C 69/22; C07C 69/34; C07C 69/675; C11C 3/006; C11C 3/04
See application file for complete search history.

(56) References Cited

U.S. PATENT DOCUMENTS

| 667,043 | A | | 1/1901 | Steep |
| 2,401,338 | A | * | 6/1946 | Dunmire ................ C11B 3/001 |
| | | | | 554/191 |
| 2,566,559 | A | * | 9/1951 | Dolnick ................ C07C 41/56 |
| | | | | 568/605 |
| 2,813,113 | A | | 11/1957 | Goebel et al. |
| 2,997,493 | A | | 8/1961 | Huber |
| 3,048,608 | A | | 8/1962 | Girard et al. |
| 4,061,581 | A | | 12/1977 | Leleu et al. |
| 4,298,730 | A | | 11/1981 | Galleymore et al. |
| 4,313,890 | A | | 2/1982 | Chu et al. |
| 5,362,368 | A | | 11/1994 | Lynn et al. |
| 5,773,256 | A | | 6/1998 | Pelenc et al. |
| 5,773,391 | A | | 6/1998 | Lawate et al. |
| 6,107,500 | A | | 8/2000 | Prossel et al. |
| 7,125,950 | B2 | | 10/2006 | Dwan'Isa et al. |
| 7,192,457 | B2 | | 3/2007 | Murphy et al. |
| 7,589,222 | B2 | | 9/2009 | Narayan et al. |
| 2004/0167343 | A1 | | 8/2004 | Halpern et al. |
| 2005/0112267 | A1 | | 5/2005 | Kian et al. |
| 2006/0194974 | A1 | | 8/2006 | Narayan et al. |
| 2009/0216040 | A1 | | 8/2009 | Benecke et al. |
| 2009/0239964 | A1 | | 9/2009 | Sasaki et al. |
| 2010/0087350 | A1 | | 4/2010 | Sonnenschein et al. |
| 2010/0117022 | A1 | | 5/2010 | Carr et al. |
| 2011/0077350 | A1 | | 3/2011 | Malotky et al. |
| 2011/0269979 | A1 | | 11/2011 | Benecke et al. |

(Continued)

FOREIGN PATENT DOCUMENTS

| AU | 165032 | 2/1954 |
| CN | 101077856 A | 11/2007 |

(Continued)

OTHER PUBLICATIONS

Handbook of Chemistry and Physics (96th Edition, 2015-2016), pp. 6-210 to 6-228.*
European Search Report for EP13755664.3 dated Apr. 28, 2015.
Akerman et al., "Biolubricant Synthesis Using Immobilised Lipase: Process Optimisation of Trimethylolpropane Oleate Production," Process Biochem. 46:2225-2231 (2011).
Translated Office Action for Chinese Application No. 201380022561.5, mailed Sep. 6, 2015.

(Continued)

*Primary Examiner* — Paul A Zucker
*Assistant Examiner* — Mark Luderer
(74) *Attorney, Agent, or Firm* — LeClairRyan, a Professional Corporation

(57) ABSTRACT

Alkyl esters (butyl, hexyl, or other) of full composition palm fatty acids, palm fatty acid distillates (PFAD), and palm kernel fatty acid distillates (PKFAD) can be used to generate polyurethane and lubricant products. The alkyl esters of the present invention can be produced via ozonolysis. The improved method for producing alkyl esters includes reacting at least one substance having at least one carbon-to-carbon double bond with ozone in the presence of least one monoalcohol that azeotropes with water. In particular, the method may comprise reacting with at least one first mole of ozone and at least one second mole of ozone, and further comprises refluxing before addition of the second mole of ozone.

28 Claims, 5 Drawing Sheets

(56) References Cited

U.S. PATENT DOCUMENTS

| | | |
|---|---|---|
| 2011/0269981 A1 | 11/2011 | Benecke et al. |
| 2011/0269982 A1 | 11/2011 | Benecke et al. |
| 2012/0184758 A1 | 7/2012 | Krull et al. |
| 2015/0005520 A1 | 1/2015 | Benecke et al. |
| 2015/0018260 A1 | 1/2015 | Benecke et al. |
| 2015/0018444 A1 | 1/2015 | Garbark et al. |
| 2015/0087850 A1 | 3/2015 | Benecke et al. |

FOREIGN PATENT DOCUMENTS

| | | |
|---|---|---|
| CN | 101812349 A | 8/2010 |
| CN | 102010772 A | 4/2011 |
| EP | 0010333 A1 | 4/1980 |
| EP | 1260497 A2 | 11/2002 |
| EP | 1529828 A1 | 5/2005 |
| EP | 1533360 A1 | 5/2005 |
| JP | S57185235 A | 11/1982 |
| JP | 04018049 A | 1/1992 |
| JP | 2008013546 A | 1/2008 |
| KR | 10-2008-0023290 A | 3/2008 |
| MY | 140833 A | 1/2010 |
| WO | 9324585 A1 | 12/1993 |
| WO | 98/50338 A1 | 11/1998 |
| WO | 00-39068 A1 | 7/2000 |
| WO | 0039068 A1 | 7/2000 |
| WO | 2004087847 A1 | 10/2004 |
| WO | 2006093874 A2 | 9/2006 |
| WO | 2007027223 A2 | 3/2007 |
| WO | 2010078491 A1 | 7/2010 |
| WO | 2010078493 A1 | 7/2010 |
| WO | 2010078498 A1 | 7/2010 |
| WO | 2010078505 A1 | 7/2010 |
| WO | 2010085545 A1 | 7/2010 |
| WO | 2013129907 A1 | 9/2013 |
| WO | 2013129908 A1 | 9/2013 |
| WO | 2013129909 A1 | 9/2013 |
| WO | 2013129910 A1 | 9/2013 |
| WO | 2013129911 A1 | 9/2013 |
| WO | 2014133380 A8 | 9/2014 |

OTHER PUBLICATIONS

Search Report and Written Opinion for Singapore Application No. 11201405261T, mailed Sep. 10, 2015.

Search Report and Written Opinion for Singapore Application No. 11201405268P, mailed Oct. 1, 2015.

Ackman et al., "Ozonolysis of Unsaturated Fatty Acids. I. Ozonolysis of Oleic Acid," Can. J. Chem., 39:1956-1963 (1961).

Yunus et al., "Preparation and Characterization of Trimethylolpropane Esters from Palm Kernel Oil Methyl Esters," J. Oil Palm Research, 15(2):42-49 (2003).

Spyros, A., "Quantitative Determination of the Distribution of Free Hydroxylic and Carboxylic Groups in Unsaturated Polyester and Alkyd Resins by 31 P-NMR Spectroscopy," J. Appl. Polym. Sci., 83:1635-1642 (2002).

PCT International Search Report and Written Opinion for International Patent Application No. PCT/MY2013/000038 (Jun. 27, 2013).

PCT International Search Report and Written Opinion for International Patent Application No. PCT/MY2013/000039 (Jun. 27, 2013).

PCT International Search Report and Written Opinion for International Patent Application No. PCT/MY2013/000040 (Jun. 28, 2013).

PCT International Search Report and Written Opinion for International Patent Application No. PCT/MY2013/000041 (Jun. 28, 2013).

PCT International Search Report and Written Opinion for International Patent Application No. PCT/MY2013/000042 (Jun. 28, 2013).

International Preliminary Report on Patentability for International Patent Application No. PCT/MY2013/000038 (Sep. 12, 2014).

International Preliminary Report on Patentability for International Patent Application No. PCT/MY2013/000039 (Sep. 12, 2014).

International Preliminary Report on Patentability for International Patent Application No. PCT/MY2013/000040 (Sep. 12, 2014).

International Preliminary Report on Patentability for International Patent Application No. PCT/MY2013/000041 (Sep. 12, 2014).

International Preliminary Report on Patentability for International Patent Application No. PCT/MY2013/000042 (Sep. 12, 2014).

Ackman et al., 'Ozonolysis of Unsaturated Fatty Acids,' Can. J. Chem. 39:1956-1963 (1961).

International Search Report and Written Opinion for PCT/MY2013/000038 mailed Jun. 27, 2013.

Third Party Submission for U.S. Appl. No. 14/381,554, dated Jul. 13, 2015.

Extended European Search Report for EP13755362.4 dated Aug. 21, 2015.

Extended European Search Report for EP13754711.3 dated Sep. 3, 2015.

PCT International Search Report and Written Opinion corresponding to PCT/MY2014/000026, filed Feb. 28, 2014 (mailed May 21, 2014).

Office Action for China Application No. 201380022561.5 (Apr. 18, 2016).

Sebedio et al., "Comparison of the Reaction Products of Oleic Acid Ozonized in BCI3-, HCI- and BF3-MeOH Media," Chemistry and Physics of Lipids 35(1):21-28 (1984) (Abstract only).

Office Action dated Aug. 2, 2016 for U.S. Appl. No. 14/381,554.

Extended European Search Report for EP14756526.1 (Sep. 19, 2016).

Chinese Office Action for Chinese application CN 201480024193.2 (Aug. 17, 2016) (with English Translation attached).

* cited by examiner

METHOD FOR THE PRODUCTION OF ESTERS AND USES THEREOF

This application is a national stage application under 35 U.S.C. 371 from PCT/MY2013/000038, filed Feb. 28, 2013, which claims the benefit of U.S. Provisional Patent Application Ser. No. 61/604,267, filed Feb. 28, 2012, each of which is hereby incorporated by reference in its entirety.

FIELD OF THE INVENTION

The present invention relates to methods for the preparation of esters, in particular alkyl esters and/or ester alcohols.

BACKGROUND OF THE INVENTION

Ester alcohols, in particular, ester polyols are very useful for the production of polyurethane-based coatings and foams, as well as, polyester applications. The present invention provides a process using renewable resources, such as, oils and fats, fatty acids, and fatty acid esters derived from plants and animals to produce polyurethane foams and lubricants. Further, sources having a carbon-carbon double bond, such as, hydrocarbons, petrochemical, fossil fuel, crude oil and the like may be used in the formation of the ester alkyls. For example, oleochemicals are chemicals that are derived from plants and animal fats. Oleochemicals are analogous to petrochemicals, which are chemicals derived from petroleum. As the price in crude oil increases, there is an increase in demand from oleochemical substances.

Conventionally, ester polyols are produced from animal or vegetable fats using ozonolysis. Organic solvents are used as a solvent in ozonolysis to control the reactivity of the intermediate. The addition of water found in organic solvents suppresses the formation of unwanted byproducts in the intermediates. However, if the ozonolysis is an oxidative process, ketones or carboxylic acids are formed. A disadvantage of this process is that more ozone must be added in the second ozonolysis step to convert the ketones or aldehydes to acids than in the first ozonolysis step.

In a two-stage ozonolysis method of producing polyols from fats or oils, the aldehyde was converted to an acetal, which was then converted by ozone to an ester. PCT Application No. PCT/US2006/016022 (Pub. No. WO2007027223) describes various solvent-based approaches to prepare product ester polyols. One approach involves a two-stage ozonolysis process for the production of product ester polyols where soybean oil is subjected to ozonolysis in the presence of primary polyols, such as, glycerin and a solvent.

In this process, two moles of ozone are required per mole of starting material double bond where the first mole of ozone initially reacts with the double bonds of the starting material to form molozonide intermediates. A molozonide is an unstable cyclic organic compound.

The molozonides dissociate to form carbonyl oxide and aldehyde intermediates. The carbonyl oxide intermediates are trapped with primary polyols, such as, glycerin to produce alkoxy hydroperoxide functionality. The primary polyols also react with the aldehyde functionality produced during the dissociation of the molozonide to produce cyclic acetals and water in an equilibrium process.

A second mole of ozone is then added to convert the cyclic acetals to ester polyols via hydrotrioxides intermediates in a process that occurs at an ambient temperature. The procedure is then completed by heating the reaction mixture, typically by refluxing the solvent, to convert alkoxy hydroperoxides to ester polyols. The main role of the solvent is to provide heat dissipation and cosolubilization of different types of reactants. Most organic solvents have little or no water. However, if water is present, water can react with certain intermediates to form unwanted products.

A variation of the above approach involves the substitution of monoalcohols for primary polyols to form carboxylic esters rather than ester polyols. Carboxylic esters can be converted to ester polyols by transesterification with primary polyols.

However, there still is a need in this technical field for improved methods for the preparation of ester alcohols, particularly with methods that increase the yield of ester alcohols while more efficiently using ozone. Therefore, the present invention seeks to improve the rate of incorporation and delivery of gaseous ozone that is bubbled through the reaction mixture during addition of the second mole of ozone.

The approach and methodology as proposed in the present invention provides a solution with respect to increasing the yield of esters relative to the amount of delivered ozone from a substance having at least one carbon-to-carbon double bond during ozonolysis. The ozonolysis of the double bond forms an aldehyde. An aspect of the present invention includes reacting the aldehyde with a monoalcohol to form an acetal and produce water.

Further, a feature of the present invention includes a refluxing step to remove water formed during the reaction of the aldehyde with the monoalcohol to form an acetal and during reflux from the substance having at least one carbon-to-carbon double bond before performing another ozonolysis reaction. The primary polyols are not subjected to direct oxidation by exposure to ozone because the primary polyols are only used in the subsequent transesterification process. Therefore, the primary polyols are not exposed to ozone.

Another advantage of the present invention is that it uses less expensive feedstock, such as, palm fatty acid distillate (PFAD) and full composition fatty acids that do not require fractionation. PFAD is generally sold for industrial uses and non-food applications. PFAD is a byproduct of palm oil production and potentially viewed as a source of biodiesel. In another aspect of the present invention, sources having a carbon-carbon double bond, such as, hydrocarbons, petrochemical, fossil fuel, crude oil and the like may be used in the formation of the ester alkyls.

The subject matter claimed herein is not limited to embodiments that solve any disadvantages or that operate only in environments such as those described above. Rather, this background is only provided to illustrate on exemplary technology area where some embodiments described herein may be practiced.

SUMMARY OF THE INVENTION

The present invention provides an improved method for producing an ester, in particular, alkyl esters and/or ester alcohols.

According to a first aspect, the present invention provides a method for producing at least one ester comprising reacting at least one substance having at least one carbon-to-carbon double bond with ozone in the presence of at least one monoalcohol that azeotropes with water or a monoalcohol and a solvent that also azeotropes with water. If the monoalcohol that azeotropes with water is used alone, the monoalcohol must be relatively insoluble in water in order to obtain phase separation with water upon condensation after the distillation.

In particular, the substance having at least one carbon-to-carbon double bond may comprise biobased oils, fats, fatty acids, fatty acid esters, and the like.

In particular, the method according to the invention comprises reacting with at least one first mole of ozone and at least one second mole of ozone, and further comprises refluxing before the addition of the second mole of ozone. More in particular, the method according to the present invention comprises reacting with at least one first mole of ozone and at least one second mole of ozone, and further comprises refluxing and removing water by azeotropic distillation before adding the second mole of ozone.

According to a particular aspect, the present invention provides a method for producing an ester comprising the use of a monoalcohol that azeotropes with water that comprises at least one monoalcohol with at least four carbon atoms. In particular, the monoalcohol that azeotropes with water comprises 1-butanol.

According to a particular aspect of the invention, in the method according to the invention, the monoalcohol may be used in the presence of at least one solvent that also azeotropes with water. In particular, the method may comprise the addition of at least a first mole and a second mole of ozone, and further comprises refluxing in the presence of at least one solvent that azeotropes with water before adding the second mole of ozone.

Further, the present invention also provides at least one ester polyol obtained or obtainable from a method according to any aspect of the invention. There is also provided an article of manufacture comprising the ester polyol according to the invention. There is also provided a coating or foam comprising the ester polyol according to the invention.

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

DETAILED DESCRIPTION OF THE INVENTION

The present invention relates to a method for producing at least one ester comprising reacting at least one substance having at least one carbon-to-carbon double bond with ozone in the presence of least one monoalcohol that azeotropes with water. In particular, the substance having at least one carbon-to-carbon double bond may comprise biobased oils, fats, fatty acids, fatty acid esters, and the like.

The method of the present invention may also be referred to as an 'ozonolysis reaction' as used herein the description.

The term 'comprising' as used in the context of the invention refers to where the various compounds, components, ingredients, or steps, can be conjointly employed in practicing the present invention. Accordingly, the term 'comprising' encompasses the more restrictive terms 'consisting essentially of', 'consisting of' and 'having'. With the term 'consisting essentially of' it is understood that the method of the present invention 'substantially' comprises the indicated compound, component, ingredient or step as 'essential' element.

Figure 1:
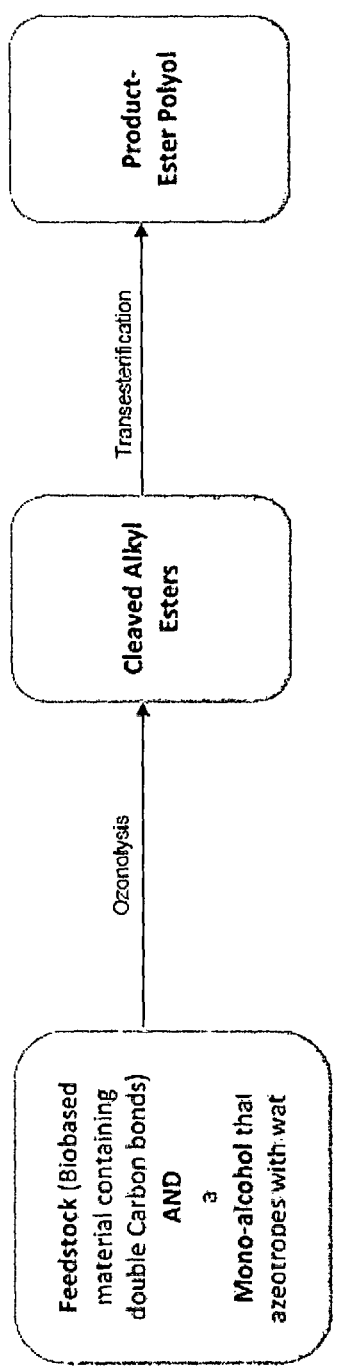
FIG. 1 is a simplified block diagram illustrating the general process of producing ester alcohols via the step of ozonolysis of a substance having at least one carbon-to-carbon double bond to form cleaved alkyl esters, followed by the transesterification of the alkyl esters to form the ester alcohols.
Figure 4:
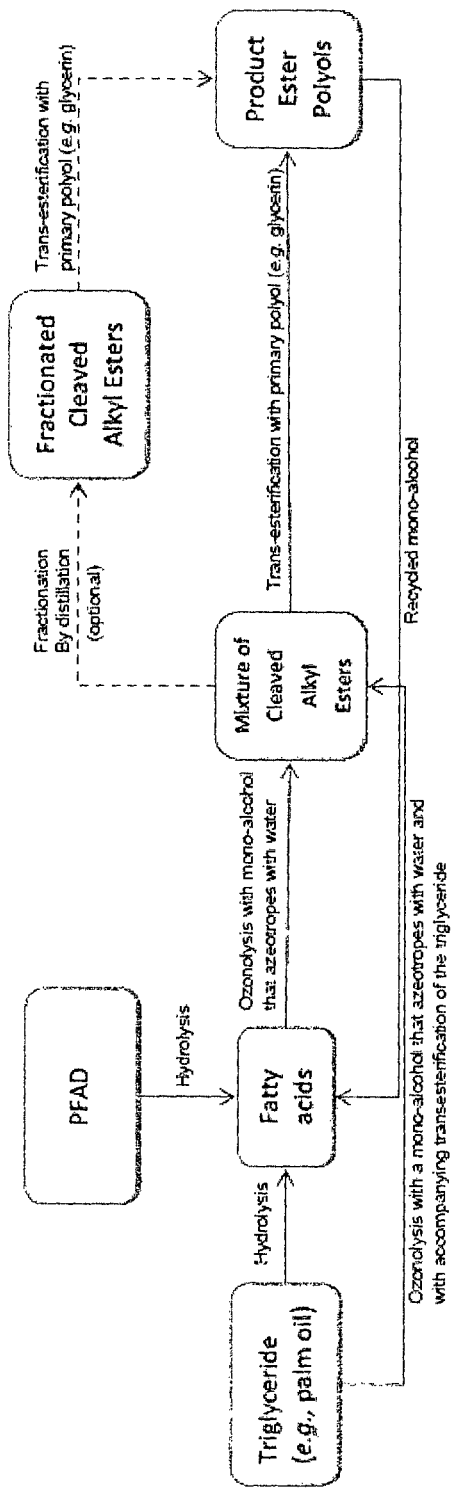
FIG. 4 is a flowchart illustrating the process of producing product ester polyols from triglycerides (e.g., palm oil) and/or palm fatty acid distillates (PFAD) via the step of ozonolysis of fatty acids in the presence of a monoalcohol that azeotropes with water into a mixture of cleaved alkyl esters (or ozone esters), followed by the optional step of fractionation by distillation of the mixture of ozone esters, and transesterification in the presence of a polyol (e.g., glycerin).
Figure 5:
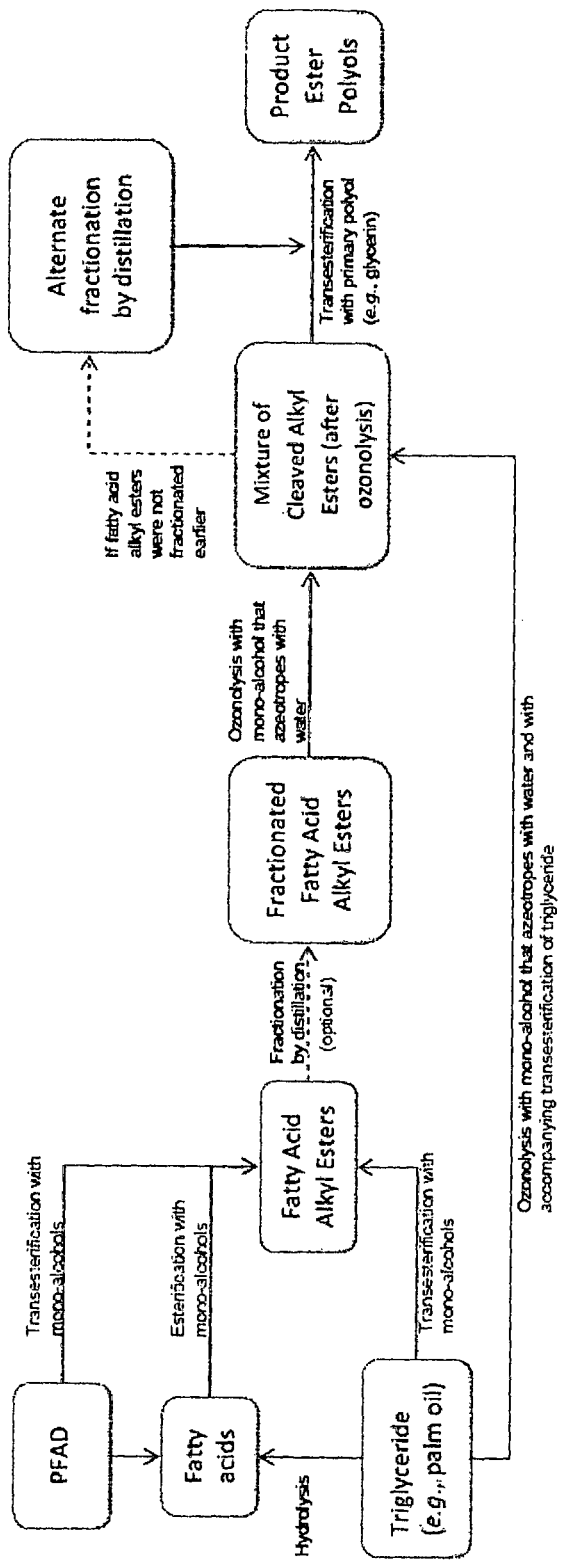
FIG. 5 is a flowchart illustrating the process of producing product ester alcohols, in particular, ester polyols from triglycerides (e.g., palm oil) and/or PFAD via the step of esterification/transesterification with monoalcohols of fatty acids/triglycerides to form fatty acid alkyl esters, followed by optional fractionation by distillation, and followed by ozonolysis of the optionally fractionated fatty acid alkyl esters in the presence of a monoalcohol that azeotropes with water into a mixture of cleaved ozone esters, and then transesterification in the presence of a polyol (e.g., glycerin). Optionally, if the fatty acid alkyl esters were not fractionated before, an alternate step of fractionation by distillation is performed prior to the transesterification with glycerin.

The term 'feedstock' used herein the specification, including FIG. 1, FIG. 4 and FIG. 5 is understood to mean any substance having at least one carbon-to-carbon double bond as defined herein the specification. The term feedstock also refers to any alkene or olefin comprising at least one carbon-to-carbon double bond, as shown in, for example, FIG. 2.

The phrase 'substance having at least one carbon-to-carbon double bond' used herein the present invention may comprise any biobased or non-biobased substance, compound, and/or material having at least one carbon-to-carbon double bond. The term 'substance', 'compound,' and/or 'material' may be used interchangeably herein the present invention. Even more in particular, the biobased substance may comprise at least one alkene. An alkene is defined for the purpose of the present invention as an organic compound consisting of hydrogen and carbon atoms where there is at least one carbon-hydrogen double bond. The alkene may be a biobased or non-biobased substance and/or compound. In particular, alkenes are unsaturated hydrocarbons and are also called olefins.

The term 'biobased substance' used herein in the present invention may be understood to mean any substance, compound, and/or material that may be derived from any living matter and may comprise at least one carbon-to-carbon double bond. In particular, the biobased substance may comprise any lipids, waste biomass, biobased products, vegetable oil, animal fat, fatty acids, and/or fatty acid esters, and the like.

The term 'fatty acid' is understood to mean any carboxylic acid (—COOH) with a long aliphatic chain, which may be saturated or unsaturated. For example, fatty acids may be derived from the hydrolysis of triglycerides or phospholipids. In particular, the fatty acid may be selected from the group consisting of: palm fatty acids, palm kernel fatty acid distillate, tallow fatty acids, fractionated tallow fatty acids, fractionated palm fatty acid distillate, and fractionated palm kernel fatty acid distillate and fatty acids of the soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, fish oil, algae oil, wheat germ oil, soya oil, hemp oil, or the like and a mixture thereof.

The 'fatty acid esters' may, but are not limited to, be obtained by transesterification of lipids or esterification of fatty acids obtained by hydrolysis of triglycerides, or any other methods known in the art.

The term 'lipids' used herein in the present invention is understood to mean any organic compounds comprising at least a chain of hydrocarbons, including, but are not limited to, vegetable oils, animal fats, fatty acids, fatty acid esters and the like. For example, lipids may comprise triglycerides.

Triglycerides are esters, which may be derived from a glycerol molecule and three molecules of fatty acids. Suitable examples of triglycerides include vegetable oil and animal fat. In particular, the triglyceride may be selected from soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, algae oil, wheat germ oil, soya oil, hemp oil, fish oil, tallow, duck fat, butter, or the like and a mixture thereof.

Lipids may also encompass glyceride molecules, such as, fatty acids and their derivatives, including fatty acid esters. Suitable examples of lipids include, but are not limited to, palm oil, palm oil fatty acids, olein, olein fatty acids, soybean oil, tallow, tallow fatty acids, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, fish oil, algae oil, wheat germ oil, soya oil, and hemp oil.

Byproducts of the above-mentioned oils and lipids, such as, palm fatty acid distillates (PFAD), palm kernel fatty acid distillates, fractionated palm fatty acid distillate, and fractionated palm kernel fatty acid distillate, fatty acids of soybean oil, palm fatty acid alkyl esters, alkyl esters of any biobased oils or fats, or the like, or a mixture, or a fraction thereof are also used as the biobased substance. In a particular aspect of the present invention, the substance having at least one carbon-to-carbon double bond may comprise a lipid.

In particular, the substance having at least one carbon-to-carbon double bond may be a vegetable oil. More particularly, the substance having at least one carbon-to-carbon double bond may be palm oil or palm olein.

In a further aspect, the substance having at least one carbon-to-carbon double bond may comprise a fatty acid ester. In particular, the fatty acid ester may be a palm fatty acid alkyl ester.

Non-biobased substance used herein in the present invention may be understood to mean any substance comprising a compound, material and/or matter that are not derived from any living matter, and having at least one carbon-to-carbon double bond. In particular, the non-biobased substance may be synthesized from hydrocarbon, petrochemical, fossil fuel, crude oil, and the like. Even more in particular, the non-biobased substance may comprise at least one alkene.

A minimum boiling azeotrope is understood to mean a mixture of two or more components whose boiling point is lower than that of either component where the azeotrope distillate composition is a constant composition that is not related to the composition of the boiling components. A monoalcohol that azeotropes with water is understood to mean any monohydric alcohol (i.e., having only one hydroxyl group) that forms a minimum boiling azeotrope composition with water. For example, the azeotropic distillate composition of ethanol/water is close to a ratio of 96/4 and that of 1-butanol/water is close to a ratio of 57.5/42.5, regardless of their respective solution compositions, as long as, both components remain in the distillation vessel.

The monoalcohol that azeotropes with water may be selected from the group including: 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers, 1-tetradecanol or isomers thereof, cetyl alcohol or isomers thereof, and stearyl alcohol or isomers thereof.

In particular, the present invention relates to the method of producing esters, wherein the monoalcohol that azeotropes with water comprises at least one monoalcohol with at least four carbon atoms.

More particularly, the present invention relates to the method of producing esters, where the monoalcohol that azeotropes with water to form an azeotrope composition has a high water content to facilitate effective water distillation. In particular, the water content of the azeotrope composition is from a range of 4 to 99 percent water.

For example, the water content of azeotrope of ethanol is about 4.0%. The water content of the azeotropic composition of 1-butanol is about 42.5%. The water content of the azeotropic composition of 1-hexanol is about 33.0%. The water content of the azeotropic composition of 1-octanol (boiling point: 195.0° C.) is about 90.0%. Preferably, the water content of the azeotrope composition is about 42.5-weight percent water.

More particularly, the monoalcohol that azeotropes with water, as described in the present invention, is such that water has a low solubility in the monoalcohol at ambient temperatures to allow effective phase separation with water upon condensation after distillation using conventional azeotropic separation techniques and equipment, such as, a Dean Stark or Barrett apparatus. Preferably, the monoalcohol that azeotropes with water has at least four carbon atoms. In particular, the solubility of water in the monoalcohol is less than 30 weight percent. Preferably, the solubility of water in the monoalcohol is 20.1 weight percent water or less.

In particular, the present invention relates to the method of producing esters, wherein the monoalcohol that azeotropes with water comprises at least one monoalcohol with at least four carbon atoms.

According to a particular aspect, the present invention relates to the method of producing esters where the monoalcohol that azeotropes with water comprises 1-butanol.

According to another aspect of the present invention, the monoalcohol that azeotropes with water comprises 1-hexanol.

For example, the solubility of 1-butanol in water is 6.33%. The solubility of water in 1-hexanol is 7.2% and the solubility of 1-hexanol in water is 0.59%. The boiling point of 1-butanol is 117.8° C. and the azeotropic boiling point of 1-butanol with water is 92.4° C. The boiling point of 1-hexanol is 157.1° C. and the azeotropic boiling point of 1-hexanol with water is 97.8° C. The azeotropic composition of 1-hexanol/water is close to a ratio of 67.2/32.8.

The higher azeotropic water content and lower water solubility of 1-hexanol compared to 1-butanol will result in a more effective removal of water by azeotropic distillation. Preferably, a Barrett or Dean Stark apparatus is used for azeotropic distillation. The enhanced combined properties of 1-hexanol also reduce the need to employ an auxiliary azeotropic solvent.

According to another aspect of the present invention, the ozonolysis of the substance having at least one carbon-to-carbon double bond forms an aldehyde. The aldehyde reacts with an azeotropic monoalcohol to form an acetal and water. The azeotropic solvent is a mixture of two or more substances. The two or more substances may comprise a monoalcohol or non-alcohol. The azeotropic solvent may be used with or without another azeotropic solvent. In this embodiment, the azeotropic solvent may comprise a substance that does not contain a hydroxyl, such as, an alcohol or more specifically, does not comprise a monoalcohol.

Figure 2:
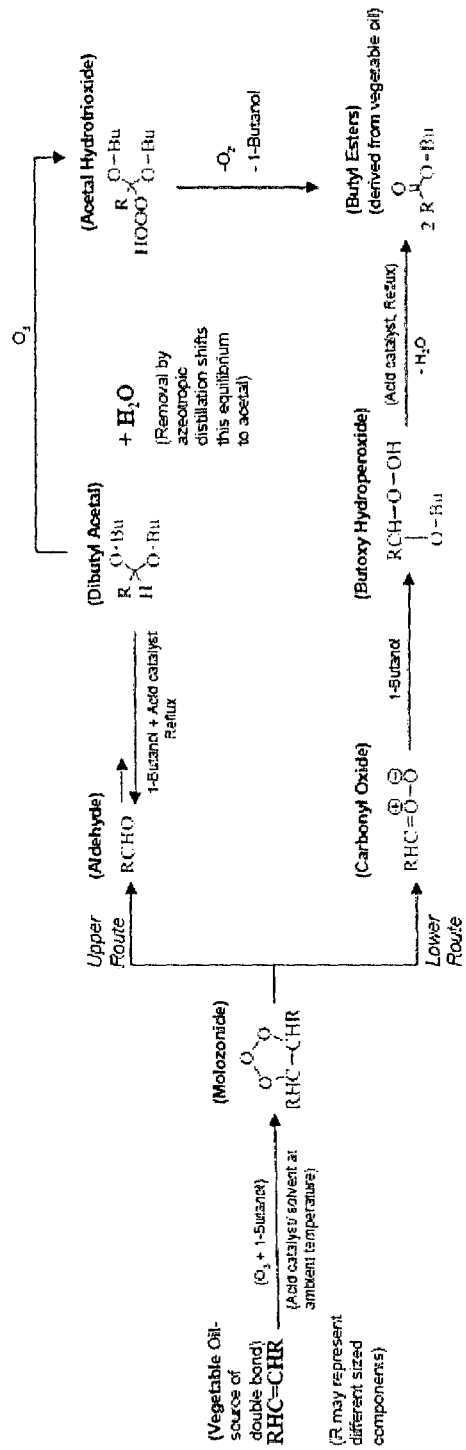
FIG. 2 is a schematic diagram illustrating a particular aspect of the invention. In particular, the reaction steps involved in the two stage ozonolysis of a generalized carbon-to-carbon double bond (e.g., vegetable oil) in the presence of 1-butanol (a monoalcohol that azeotropes with water). It is also shown that reflux is carried out before adding the second mole of ozone.

The present invention relates to the method of producing esters where the monoalcohol azeotropes with water. As shown in FIG. 2, the use of the monoalcohol that azeotropes with water shifts the equilibrium of the aldehydes towards the acyclic acetals by effective removal of water, which is the co-product of the acetal generation. Maximizing the concentration of acyclic acetals, which are the target of the second mole of ozone, leads to more effective incorporation of ozone that is administered. Accordingly, a decreased amount of ozone is needed to convert aldehydes to esters (via acetal hydrotrioxides). This leads to an improved reaction time for the ozonolysis process.

The method according to the present invention may further comprise reacting the at least one substance having at least one carbon-to-carbon double bond with ozone in the presence of least one monoalcohol that azeotropes with water, at a temperature ranging from about 5° C. to about 100° C.

In particular, the temperature of the ozonolysis reactions may range from 5° C. to 70° C. Even more in particular, the temperature may range from 15° C. to 65° C. Preferably, the temperature may range from 20° C. to 60° C.

FIG. 1 shows a simplified flowchart of converting a feedstock to cleaved alkyl esters via ozonolysis. In this embodiment, the feedstock is a biobased material. The biobased material may be derived from a palm fatty acid distillate (PFAD) of palm oil that is abundant, readily available, and does not directly compete with the food chain. PFAD is composed mainly of fatty acids but also contains monoglycerides, diglycerides and triglycerides. The biobased material containing a carbon-to-carbon double bond may also be vegetable oils, fatty acids, or fatty acid esters. The ozonolysis step uses an organic reactive solvent, such as, a monoalcohol that azeotropes with water to cleave the carbon-to-carbon double bonds of the feedstock.

If the feedstock is a triglyceride or fatty acid ester, transesterification of the original carboxylic acid sites occurs with monoalcohol during azeotropic distillation and the subsequent reflux stage to form fatty acid alkyl esters at these sites. If the feedstock is a fatty acid, esterification of the original fatty acid sites also occurs with monoalcohols at these sites. Fractionated PFAD or Emery Edenor OL 72 are used as feedstock to form cleaved butyl esters. In Example 2, fractionated PFAD and a monoalcohol (1-butanol) form cleaved butyl esters. In Example 3, Emery Edenor OL 72 and a monoalcohol plus a solvent are used to form cleaved butyl esters. The resulting cleaved alkyl esters or diesters undergo a transesterification step with a primary polyol, such as, glycerine to form product ester polyols.

As shown in FIG. 2, the present invention comprises reacting vegetable oil with at least one first mole of ozone in the presence of an acidic catalyst and solvent. Any suitable biobased or non-biobased material having at least one substance with at least one carbon-to-carbon double bond can represent the starting material and may be used interchangeably. The biobased material having at least one substance with at least one carbon-to-carbon double bond is represented by RHC=CHR where the R groups may represent different sized components. In the upper route, after refluxing, the resulting acetal reacts with at least one second mole of ozone.

According to a particular aspect, as shown in FIG. 2, the invention further comprises reacting the vegetable oil with at least one first mole of ozone and at least one second mole of ozone, and further comprises refluxing the acetal before the addition of the second mole of ozone. One of the differences between the prior art method described in the WO2007027223 and the present invention is that refluxing is carried out only after the second mole of ozone is added in WO2007027223.

Further, the method according to the present invention comprises refluxing and removing water by azeotropic distillation, before the addition of the second mole of ozone as shown in the upper route of FIG. 2.

As illustrated in FIG. 2, refluxing before the addition of the second mole of ozone: (1) shifts the aldehyde/acetal equilibrium to the acetal side, (2) partially esterifies all of the carboxylic acid functionality with the monoalcohol (e.g., 1-butanol), and (3) converts butoxy hydroperoxides (the other half of the reaction pathway shown in the lower route) to butyl esters by eliminating water.

The terms 'reflux' and 'refluxing' are used interchangeably and are understood herein in the present invention to mean to boil the reaction mixture in a vessel attached to a condenser such that the vapors continuously condense for reboiling. The term 'reflux temperature' is then understood to mean the temperature at which refluxing occurs.

In particular, the step of refluxing, before the addition of the second mole of ozone, may further comprise any means, apparatus, methods, and/or techniques to separate water from the condensed distillate obtained by azeotropic distillation. Azeotropic distillation in the present invention may include separating an azeotrope composition by distillation. For example, an azeotropic distillation may include the technique of adding another component to generate a new, lower-boiling azeotrope that is heterogeneous (i.e., producing two, immiscible liquid phases, such as, water and the condensed distillate).

For example, the step of refluxing before the addition of the second mole of ozone includes, but is not limited to, the use of a Barrett or Dean-Stark apparatus to separate water from the condensed distillate obtained by azeotropic distillation. More specifically, refluxing is carried out after all of the double bonds have been consumed by ozone in the present invention.

The method according to the present invention may be carried out in the presence of at least one suitable solvent. For example, suitable solvent(s) described in WO2007027223 or in the cited references listed under the 'Reference' section of the present application, which are herein incorporated by reference may be used.

According to a particular aspect, in the method according to the present invention, the monoalcohol may be used in the presence of at least one solvent that azeotropes with water (also referred to as an auxiliary solvent). In particular, the method comprises the addition of at least a first mole and a second mole of ozone, and further comprises refluxing in the presence of at least one solvent that azeotropes with water, before addition of the second mole of ozone.

In particular, in the present invention, the monoalcohol may be a water-soluble lower alcohol, which is miscible with water in all proportions and may be used in the presence of the auxiliary solvent. A water soluble lower alcohol is defined herein the present invention as a monoalcohol with less than four carbon atoms. Examples of water-soluble lower alcohols include, but are not limited to, 1-propanol, 2-propanol, ethanol and methanol.

In particular, the solvent that azeotropes with water is selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof.

Preferably, solvents that azeotrope with water that generate azeotrope distillate compositions have relatively high water compositions. Further, it is preferred that water is essentially insoluble in the solvent/water azeotrope composition after condensation. These combined properties allow for the efficient removal of water present after initial ozone breakthrough by refluxing the reaction mixture and separating the water from solvent in the condensate, for example, when using simple equipment such as a Barrett or Dean Stark apparatus. Ozone breakthrough corresponds to the oxidation of all available carbon double bonds.

According to this aspect of the invention, refluxing is carried out after the first ozone breakthrough (i.e., after consumption of all double bonds is complete) is observed, for the specific purpose of removing water from the reaction mixture to shift the aldehyde plus monoalcohol to form an acyclic acetal plus water equilibrium toward the acetal side. Therefore, the method according to the present invention is distinct from conventional methods because when monoalcohols are used in the presence of a solvent, ozone is added until an initial ozone breakthrough and the consumption of all double bonds is complete. Then, the second mole of ozone is added to convert any acetals present to ester functionality by reacting with monoalcohols. However, the absorption of the second mole of ozone is inefficient in the case of monoalcohols since only a small percentage of aldehyde functionality generated by the absorption of the first mole of ozone is converted to acyclic acetal functionality in conventional methods.

For instance, as shown in Comparative Example 1, when monoalcohols, such as, ethanol are used in the method according to the prior art, the total ozone delivery was much higher than theoretical (about 158% of theoretical with ethanol). This is because the rate of ozone incorporation was significantly slower than the slowest practical rate that ozone could be delivered. Further, WO2007027223 discussed refluxing the reaction mixture only after the second mole of ozone addition has been absorbed. However, absorption of the second mole of ozone in the absence of effective azeotropic distillation is relatively inefficient since ozone is mainly reactive towards the alkyl acetal functionality, which is present in low concentrations in the absence of azeotropic distillation. Thus, in the absence of an effective azeotropic distillation, the absorption of the delivered ozone is inefficient.

It is known that an azeotrope forms between ethanol and water, which contains 4% water. Further, refluxing was performed after the initial ozone breakthrough in Comparative Example 1. However, the water formed during this azeotropic distillation does not phase separate. Further, there is not an effective equilibrium shift towards acetal functionality by water removal in Comparative Example 1. In Comparative Example 1, after initial ozone breakthrough occurred, extra ozone was added in five separate stages and each addition of ozone was followed by separate reflux periods for a total ozonolysis time of 10.5 hours and total reflux time of 15 hours. Thus, the total reaction time was after initial breakthrough was 25.5 hours and the ethyl ester product was formed in only 61 percent yield. The low ethyl ester yield was due to the fact that the equilibrium between the initially formed aldehyde functionality and derived ethyl acetal functionality lies to the aldehyde side and only small amounts of acetal functionality was available for reaction with ozone. Each ozonolysis cycle could only react with the small amount of acetal functionality that was available and convert this to acetal trioxide functionality, which was further converted to ethyl ester product. By comparison, Examples 2 and 3 require less ozone in the second stage of ozonolysis when effective azeotropic distillation is performed.

Example 1

Comparative Example

Formation of Ethyl Esters of Soybean Oil with Ethanol (Performed with a Small Ozone Generator)

This procedure illustrates a conventional ozonolysis that is not benefited by azeotropic distillation. Soybean oil (80 g; 0.4091 mol double bonds; 1.0909 mol reaction sites) was dissolved in ethanol (400 mL; 6.3 equivalents) containing 98% sulfuric acid (2.33 mL; 1 mole per 25 mole reaction sites). Ozone was sparged into the reactor at 2 liters per minute for 9.5 hours at which time initial breakthrough occurred. The reaction was then refluxed for three hours. Ozone was again sparged into the reactor at 2 liters per minute at 60° C. for three hours longer and the reaction was refluxed for three hours when it was determined that acetal was still remaining. Ozone was again sparged into the reactor at 2 liters per minute at 60° C. for two hours longer and the reaction was refluxed for three hours and it was found that 16% acetal still remained. Ozone was again sparged into the reactor at 2 liters per minute for three hours longer at 60° C. and the reaction was refluxed for two hours when it was determined that 3.5% acetal still remained. Ozone was again sparged into the reactor at 2 liters per minute at 60° C. for 1 hour longer and the reaction was refluxed for two hours to determine that 2% acetal still remained. Ozone was again sparged into the reactor at 2 liters per minute at 60° C. for 1.5 hours longer and the reaction was refluxed for 2 hours.

The total ozone delivered was 157.6% of the theoretical amount of ozone based on two moles ozone needed per mole double bond. The total ozonolysis reaction time in the second stage of this reaction after breakthrough was 10.5 hours. The mixture was then dissolved in ethyl acetate (500 mL) and partitioned with 10% sodium sulfite (100 mL) in 10% ammonium hydroxide. The organic layer was partitioned with 20% brine (8×100 mL portions) and dried with magnesium sulfate. The organic layer was filtered and ethyl acetate was removed by distillation. 81.17 g of final ethyl ester product was obtained, which correlates to 61.1% yield and the product was 98.5% pure.

On the contrary, in an embodiment of the present invention, the shift to an acetal compound is significant. The reaction of a monoalcohol that azeotropes with water in the presence of a solvent that azeotropes with water during refluxing where the monoalcohol that azeotropes with water phase separates after condensation to allow for a more efficient use of the ozone that is added after the first breakthrough by first converting all, or substantially all or most of the aldehyde functionality to the maximum achievable quantity of acyclic acetals. Second stage ozonolysis occurs when ozone is added after the first breakthrough. Another advantage of the solvent-based ozonolysis of the present invention is that the appropriate azeotropic solvent increases the water removal efficiency, which leads to higher acetal concentrations. Therefore, the rate of the acetal reaction with ozone is increased in the second stage ozonolysis. Further, ozone is expensive and its efficient use reduces the overall cost of the reaction.

Specifically in Examples 2 and 3, the first ozone breakthrough corresponds to oxidation of all available double bonds. Another advantage of the solvent-based ozonolysis is that the solvents generate azeotropes that have relatively high water compositions where water is essentially insoluble in the solvent/water mixtures after condensation. Their combined properties allow for the effective removal of all water present after the first ozone breakthrough by refluxing the reaction mixture and separating the water from the solvent in the condensate tube. Water removal is required to shift the equilibrium to the acetal side and refluxing with an appropriate azeotropic solvent that effectively shifts the equilibrium to the acetal side. This results in making acyclic dibutyl acetals more available for continued ozonolysis to form cleaved alkyl esters in high yields as shown in Examples 2 and 3.

Examples 2 and 3 demonstrate that converting all aldehyde functionality to the maximum achievable quantity of acyclic acetals increases the rate of acetal reaction with ozone, thus, leading to a decreased overall use of expensive ozone. As shown below, 119.8% of the theoretical ozone was consumed when 1-butanol was used by itself in Example 2. 106.9% of the theoretical ozone was consumed when 1-butanol was used in combination with butyl acetate as an auxiliary solvent in Example 3.

Example 2

Formation of Butyl Esters with monoalcohol (1-Butanol)

This example illustrates the method according to the present invention using a monoalcohol that azeotropes with water (i.e., 1-butanol). Fractionated palm oil fatty acid distillate (250.0 g; 0.914 mol double bonds; 2.7240 mol reaction sites) was dissolved in 1-butanol (875 mL; 3.5 equivalents) containing 98% sulfuric acid (1.45 mL; 1/100 mole ratio based on reaction sites). Ozone was sparged into the reactor at 2.5 liters per minute for 3 hours at which time break-through was observed. The reaction was then refluxed using a Dean-Stark tube for 1 hour to remove water. Ozone was again sparged into the reactor at 2 liters per minute for 8 hours with half of the ozone concentration used compared to the first stage ozonolysis. The second stage ozonolysis had a total ozone delivery of 119.8% (based on two moles ozone needed per mole double bond).

The resulting mixture was then refluxed in a Dean-Stark tube in place for 1.5 hours. The mixture was then stirred with washed Amberlite IRA-67 (four equivalents based on sulfuric acid). Once the pH was at 5.5, the resin was filtered and rinsed. Tin (II) oxalate (0.12 g) was added to the mixture in order to decrease the final acid value of the product by self-esterification of residual acids formed during ozonolysis with butanol. Excess butanol was then removed by distillation and the catalyst was removed by filtration. The final butyl ester product had an acid value (AV) of 4.62 and weighed 448.83 grams (103.8% yield). The excess yield came from the formation of butyl butyrate as result of the partial oxidation of butanol to butyric acid and the subsequent esterification of these components.

The reaction time for the second stage ozonolysis is 8 hours and the total ozone delivery is 119.8%.

Example 3

Formation of Butyl Esters with monoalcohol (1-Butanol) and solvent (Butyl Acetate)

This example illustrates the method according to the present invention using a monoalcohol that azeotropes with water and 1-butanol in the presence of a solvent that azeotropes with water and butyl acetate. Emery Edenor OL 72, a mixture of fatty acids obtained by fractionation of olein by partial removal of saturated fatty acids (300 g; 1.0652 mol double bonds; 3.2186 mol reaction sites) where the olein was dissolved in 1-butanol (590 mL; 2 equivalents) and butyl acetate (295 mL) containing 98% sulfuric acid (2.30 mL; 1 mole per 75 mole reaction sites).

Ozone was sparged into the reactor at 2 liters per minute for 4.75 hours at which time break-through was observed. The reaction was then refluxed using a Dean-Stark tube for 1 hour to effect water removal. Ozone was again sparged into the reactor at 2 liters per minute for 7.5 hours longer with approximately half of the concentration of the first stage ozonolysis reaching a total ozone delivery of 106.9% (based on two moles ozone needed per mole double bond). The reaction mixture may undergo a purification process where the reaction mixture is passed through a basic resin to neutralize the ozonolysis catalyst after the ozonolysis reaction and excess reagents were then removed by distillation.

The resulting mixture was then refluxed in a Dean-Stark tube for 2 hours and then stirred with washed Amberlite IRA-67 (81 mL; 1.5 equivalents based on sulfuric acid). Once the pH was greater than 4.5, the resin was filtered and rinsed. Tin (II) oxalate (0.10 g) was added to the mixture, 1-butanol and butyl acetate were removed by distillation, and the catalyst was removed by filtration. The final butyl ester product had an acid value (AV) of 0.9 and weighed 525.42 grams (99.5% yield).

The reaction time for the second stage ozonolysis is 7.5 hours and the total ozone delivery is 106.9%.

Examples 2 and 3 show that about 120% of the theoretical ozone was consumed when 1-butanol was used by itself. About 107% of theoretical ozone was consumed when 1-butanol was used in combination with butyl acetate as an auxiliary solvent. Part of the greater than 100% ozone consumed is believed to be caused by partial oxidation of 1-butanol to butanoic acid which then went underwent esterification to produce butyl butyrate. In conclusion, Examples 2 and 3 disclose that the consumption of ozone is less than when ethanol is used, as seen in comparative Example 1. Comparative Example 1 uses ethanol that forms an azeotrope with water. However, the condensed water and ethanol do not phase separate. Thus, the water will return to the reaction mixture from the Dean Stark or Barrett tube and equilibrium shifting will not occur. Further, the reaction time is shorter in Examples 2 and 3 because of the effectiveness of the azeotropic water removal using a solvent that forms an azeotrope with water which then phase separates after condensation.

Another aspect according to the present invention is including a step of refluxing after the addition of the second mole of ozone, as shown in FIG. 2. The step of refluxing after the addition of the second mole of ozone in the present invention serves to: (1) complete the conversion of all carboxylic acid functionality to butyl esters, and (2) complete the conversion of acetal hydrotrioxides to butyl esters by elimination of oxygen. When effective azeotropic distillation is performed, less ozone is required and the reaction times are significantly faster than the conventional ozonolysis methods.

In particular, the refluxing occurs immediately after the initial ozone breakthrough when effective azeotropic distillation is performed with ozonolysis. One preferred azeotropic solvent is ethyl isobutyrate.

Particularly, the monoalcohol that azeotropes with water is 1-butanol and the solvent azeotropes with water is ethyl isobutyrate or butyl acetate.

The solubility of water in 1-butanol and butyl acetate is 20.1-weight percent water and 3.3 weight percent water, respectively. The 1-butanol/water azeotrope composition, and the butyl acetate/water azeotrope composition has a water content of 42.5 weight percent water and 28.7 weight percent water, respectively.

Further, butyl acetate and 1-butanol are soluble in each other such that the use of these two components in azeotropic distillation results in a 1-butanol/butyl acetate phase where water has low solubility. The solvents are more effective at water partitioning versus using 1-butanol alone that has a water solubility of about 20.1%, thus, resulting in the effective removal of water from the reaction mixture.

The equilibrium between aldehydes and monoalcohols, such as, 1-butanol to form acyclic acetals lies on the aldehyde side, as indicated by the reaction arrows (⇌) shown in FIG. 2 (upper route). Therefore, water removal is required to shift the equilibrium to the acetal side. Refluxing with a solvent that azeotropes with water effectively shifts this equilibrium to the acetal side. Because of the equilibrium shifting, the acyclic dibutyl acetals are available for continued ozonolysis to form esters in high yields. Accordingly, the ester yield is 103.8% and 99.5% in Examples 2 and 3, respectively. The increased yield in Example 2 is a result of oxidation of butanol to butanoic acid and its subsequent esterification.

According to another aspect of the present invention, the substance having at least one carbon-to-carbon double bond may be reacted in the presence of an ozonolysis catalyst. The ozonolysis catalyst may be a Lewis or Bronsted acid. Examples of ozonolysis catalysts suitable for use in the present invention are described in WO2007027223. The examples of ozonolysis catalysts include, but are not limited to, sulfuric acid, boron trifluoride, boron trichloride, boron tribromide, tin halides (e.g., tin chlorides), aluminum halides (e.g., aluminum chlorides), zeolites (solid acid), molecular sieves (solid acid), phosphoric acid, boric acid, acetic acid, and hydrohalic acids (e.g., hydrochloric acid). The above-mentioned acid catalysts, such as, sulfuric acid are readily available and inexpensive.

The ozonolysis catalyst can also be a resin-bound acid catalyst. Examples of resin-bound acid catalysts include, but are not limited to, Silicycle propanesulfonic acid, montmorillonite, or Amberlite® IR-120 (macroreticular or cellular resins or silica covalently bonded to sulfonic acid or carboxylic acid groups).

In a preferred embodiment of invention, the ozonolysis catalyst for use in the method of the present invention comprises sulfuric acid.

In the method according to the present invention, the produced ester is at least one alkyl ester that is further transesterified in the presence of at least one primary polyol to produce at least one ester polyol. A primary polyol used in the present invention is a compound and/or alcohol containing more than one hydroxyl group.

Figure 3:
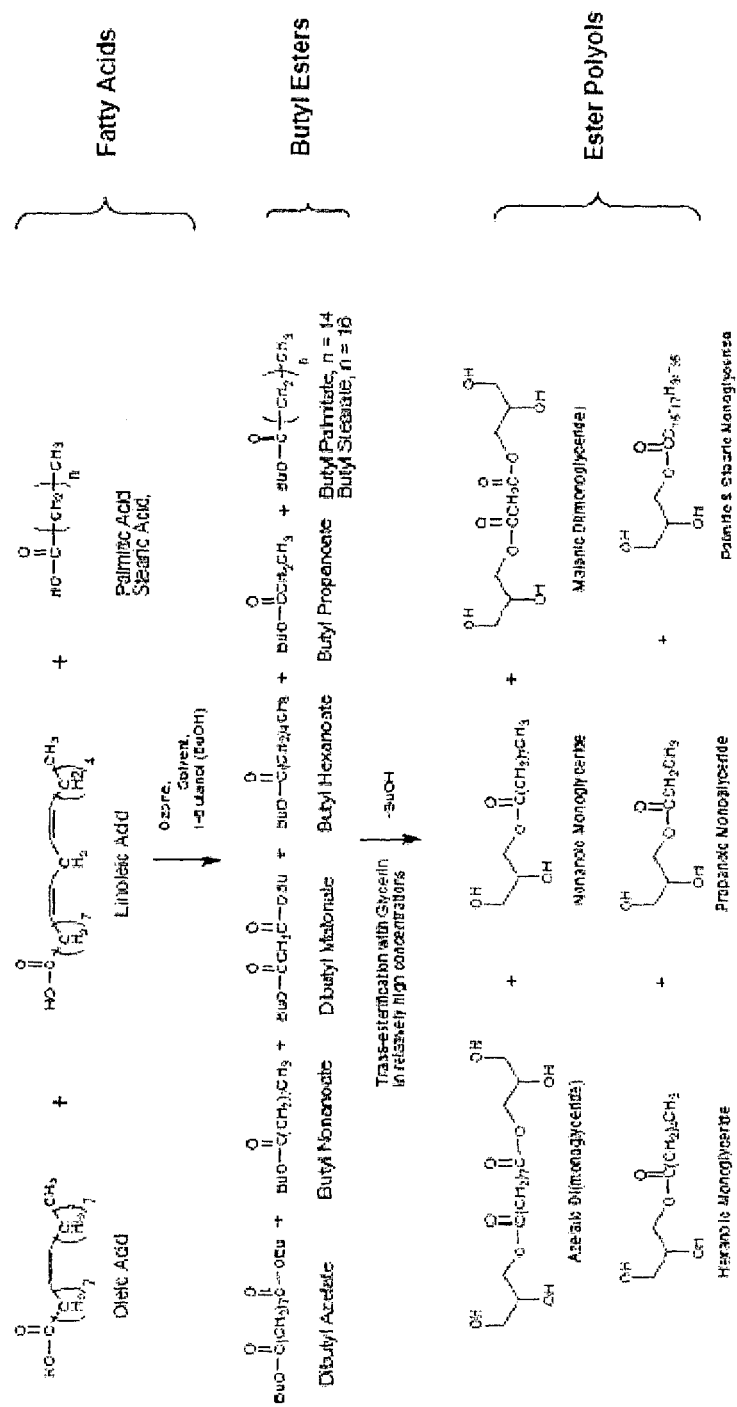
FIG. 3 is a schematic diagram illustrating butyl esters that are formed from the major fatty acids derived from palm-based feedstock when they undergo ozonolysis and esterification in the presence of 1-butanol, followed by transesterification of the butyl esters into ester polyols in the presence of a polyol (glycerin). In a particular example, the palm-based feedstock may be a non-fractionated palm oil where the fatty acid composition of the non-fractionated palm oil includes oleic acid (41%), linoleic acid (10%), palmitic acid (42%), stearic acid (4%), and other fatty acids.

Reference is now made to FIG. 3. FIG. 3 shows the formation of individual butyl esters from the major fatty acids derived from palm-based feedstock when they undergo ozonolysis in the presence of 1-butanol. An example of a palm-based feedstock is palm oil, which is a non-fractionated palm fatty acid. Some of our derived products may be high performers when at full composition or without fractionation. However, partial or full fractionation may be required for fatty acid feedstock.

FIGS. 4 and 5 show the fractionation of a mixture of cleaved alkyl esters after ozonolysis. Additionally, FIG. 5 shows fractionation by distillation of fatty acid alkyl esters. Lubricants derived from palm sources require fractionation whereas some polyols also require fractionation.

An advantage of using palm-based feedstock is the reduced cost for the overall reaction due to their lower price. Palm oil is composed of fatty acids including oleic, linoleic, palmitic, and stearic acids, as shown in FIG. 3. The ozonolysis of the palm oil is in the presence of a solvent and forms butyl esters.

The butyl esters effectively then undergo transesterification reactions with primary polyols, such as, glycerin and mixtures of primary polyols when using a tin transesterification catalyst to form the product ester alcohols, in particular ester polyols. The butyl esters may be selected from the group comprising of Dibutyl azelate, Butyl nonanoate, Dibuytyl malonate, Butyl hexanoate, Butyl propanoate, Butyl palmitate, and/or Butyl stearate, as shown in FIG. 3.

When relatively high concentrations of primary polyols are used, relatively low molecular weight product ester polyols are expected to be formed, as shown in FIG. 3. The low molecular weight product ester polyols are selected from the group comprising Azelaic di(monoglyceride), Nonanoic monoaglyceride, Malonic di(monoglyceride), Hexanoic monoglyceride, Propanoic monoglyceride, Palmitic monoglyceride, and Stearic monoglyceride. Alternatively, when relatively low concentrations of primary polyols are used, appreciably higher molecular weight product ester polyols will be formed.

In particular, the primary polyol may be selected from the group comprising of glycerin, trimethylolpropane, pentaerythritol, 1,2-propylene glycol, 1,3-propylene glycol, 2-methyl-1,3-propanediol, 1,4-butanediol, ethylene glycol, glucitol, fructose, glucose, sucrose, aldoses, ketoses, alditols, disaccharides, or combinations thereof.

According to the present invention, a basic neutralization agent is usually required to neutralize the ozonolysis catalyst after the ozonolysis reaction. Examples of the basic neutralization agent include, but are not limited to, Amberlite®

IRA-67; basic salts, such as, sodium bicarbonate, potassium bicarbonate, sodium carbonate, and potassium carbonate; amines; and polyamines. A solid ion-exchange resin, such as, Amberlite® IRA-67 is preferred to neutralize the acid catalyst because washing of the reaction mixture after ozonolysis is not required, which results in a nearly quantitative yield of product polyol.

Further, the present invention also provides at least one ester polyol obtained or obtainable from the method according to any aspect of the invention.

The present invention also relates to an article of manufacture comprising the ester polyol according to the present invention. The article of manufacture may be used for, but not limited to, polyurethane based applications, polyester applications and lubricants.

The present invention also relates to a coating or foam comprising the ester polyol according to the invention. For example, the coating or foam may include a polyurethane coating or foam produced from the ester polyol according to the invention.

Reference is now made to FIG. 4. FIG. 4 illustrates the process of producing product ester alcohols (in particular, ester polyols) from triglycerides (e.g., palm oil) and/or palm fatty acid distillates (PFAD) via the step of ozonolysis of fatty acids in the presence of a monoalcohol that azeotropes with water to form a mixture of cleaved alkyl esters (or ozone esters).

If triglycerides, fatty acids, or mixtures of glycerides and fatty acids, such as, palm fatty acid distillate (PFAD) are used as the starting material, an optional step of fractionation by distillation of the mixture of cleaved alkyl esters, and transesterification in the presence of a polyol (e.g., glycerin) is performed. As shown in FIG. 4 by the dashed line, the optional fractionation by distillation of the mixture of cleaved alkyl esters is performed to produce fractionated cleaved alkyl esters.

The hydrolysis of triglycerides forms fatty acids, which are then subjected to ozonolysis to produce cleaved alkyl esters, also known as ozone esters. The ozonolysis of fatty acids is also accompanied by esterification of the original fatty acid sites with monoalcohols at these sites during azeotropic distillation and further heating. Cleaved alkyl esters can be formed directly from triglycerides via a step of ozonolysis in the presence of a monoalcohol that azeotropes with water, as shown in FIG. 4. The ozonolysis of triglycerides is accompanied with a transesterification step at the original carboxylic acid sites during azeotropic distillation and further heating to produce the mixture of cleaved alkyl esters. The mixture of cleaved alkyl esters obtained from triglycerides is then fractionated to produce fractionated alkyl esters. The mixture of fractionated alkyl esters then undergoes a transesterification process with a primary polyol, such as, glycerine to produce the product ester polyols. The product ester polyols are selected from the group comprising Azelaic di(monoglyceride), Nonanoic monoaglyceride, Malonic di(monoglyceride), Hexanoic monoglyceride, Propanoic monoglyceride, Palmitic monoglyceride, and Stearic monoglyceride.

In another embodiment, palm fatty acid distillates (PFAD) may be used as a starting material or feedstock and source of fatty acids. The fatty acids were subject to ozonolysis with a monoalcohol that azeotropes with water to produce a mixture of alkyl esters. The monoalcohol that azeotropes with water may be used with or without another azeotropic solvent. Depending on the amount of water removed during the azeotropic distillation, ozone can be used in lower amounts to convert the fatty acids to alkyl esters.

Reference is now made to FIG. 5. FIG. 5 illustrates the process of producing product ester alcohols from fatty acids where triglycerides and/or PFAD are the source of the fatty acids. The fatty acids are esterified with monoalcohols to produce fatty acid alkyl esters.

In another embodiment, triglycerides, such as, palm oil are transesterified with monoalcohols to produce the fatty acid alkyl esters. In yet another embodiment, the mixture of cleaved alkyl esters can also be produced from the ozonolysis of triglycerides in the presence of a monoalcohol that azeotropes with water. The ozonolysis of triglycerides is accompanied with a transesterification step to produce the mixture of cleaved alkyl esters.

In yet another embodiment, fatty acid alkyl esters are produced from converting PFAD directly via transesterification with monoalcohols. The fatty acid alkyl esters are then fractionated by distillation, as shown by the dashed line in FIG. 5. Accordingly, the fatty acid alkyl esters are fractionated into different groups of saturated fatty acids.

The resulting fractionated fatty acid alkyl esters undergo an ozonolysis reaction with a monoalcohol that azeotropes with water. The monoalcohol that azeotropes with water facilitates the removal of water from the reaction through distillation. After ozonolysis, the mixture of cleaved alkyl esters is transesterified with a primary polyol (e.g., glycerine) to produce ester polyols.

An alternate fractionation by distillation of the mixture of cleaved alkyl esters is performed if the fatty acid alkyl esters were not fractionated in an earlier step, as shown in FIG. 5 (dashed line).

Example 4

Formation of Polyol

This example illustrates the conversion of a specific collection of butyl esters to a product ester polyol. These butyl esters were obtained by ozonolysis of a mixture of oleic acid (70.0%), linoleic acid (12.9%), linolenic acid (2.76%), palmitic acid (11.1%) and stearic acid (3.19%), believed to closely represent fractionated PFAD, in the presence of 1-butanol by the previously described approach. These butyl esters (224.42 g; 1.4144 mol acid esters) were combined with glycerin (73.87 g), sorbitol (43.60 g), 2-methyl-1,3-propanediol (8.93 g), hexanoic acid (24.64 g), tin (II) oxalate (0.20 g), and dibutyltin dilaurate (0.57 g). The reaction mixture was heated slowly with mechanical stirring to 210° C. until no further distillate was obtained, which took approximately 1.5 hours. The mixture was then heated to 210° C. with a 0.5 standard cubic foot per hour (SCFH) sparge of argon for 6.25 hours.

The final ester polyol weighed 256.80 g (97% yield) and it had an acid value (AV) of 0.9 and a hydroxyl value (HV) of 392.3. The total mass balance was 98.5%.

Example 5

Formation of Intermediate Cleaved Hexyl Esters from Fatty Acid Alkyl Esters

This example illustrates the conversion of methyl olein to 1-hexyl ozone esters. Methyl olein (100.03 g; 0.3527 mole methyl esters and 0.2010 mol double bonds) was mixed with 1-hexanol (198.32 g; 1.9411 moles) and sulfuric acid, 98% (0.40 mL; 0.0075 mole). The mixture reacted with ozone in a round bottom flask containing a thermocouple, Barrett tube, and condenser while employing magnetic stirring.

Ozone was sparged into the reaction vessel until ozone breakthrough was achieved. At this point, ozone was stopped and the mixture refluxed for 30 minutes.

After refluxing, additional ozone was added and this step was followed by another 30 minute reflux when it was determined by $^1$H NMR that no acetal remained, at which point 100.6% of theoretical ozone had been added. Amberlite IRA-67 (15 mL; 1.5 equivalents with respect to total sulfuric acid protons) was added and stirred in the reaction flask for 2 hours after which time the mixture pH was found to be neutral. The mixture was then filtered and stripped on a Kugelrohr vacuum distillation apparatus for 2 hours at 70° C. at 160 micron mercury pressure. The final product mixture weighed 259.40 g and was determined by $^1$H NMR spectroscopy to be 63.4 percent by weight product with the remaining being 1-hexanol which corresponds to a 99.7% yield of 1-hexyl ozone esters.

Example 6

Formation of Intermediate Cleaved Hexyl Esters from Triglycerides

This example illustrates the conversion of palm oil to 1-hexyl ozone esters. Palm oil (100.51 g; 0.3582 mole fatty acid and 0.1934 mol double bonds) was mixed with 1-hexanol (203.78 g; 1.9945 moles) and sulfuric acid, 98% (0.40 mL; 0.0075 mole). The reaction mixture reacted with ozone in a round bottom flask containing a thermocouple, Barrett tube, and condenser while employing magnetic stirring. Ozone was sparged into the reaction vessel until ozone breakthrough was achieved. At this point, ozone was stopped and the mixture refluxed for 30 minutes.

After refluxing, more ozone was added to the mixture and reacted, which was followed by a 30 minute reflux when it was determined by $^1$H NMR that no acetal remained (at which point 104.9% of theoretical ozone had been added). Amberlite IRA-67 (15 mL; 1.5 equivalents with respect to acidic protons of sulfuric acid) was stirred in the reactor for 2 hours in which the mixture pH was neutral. The mixture was then filtered. The final product mixture weighed 349.51 g and was determined by $^1$H NMR spectroscopy to be 52.5 percent by weight product with the remaining material being 1-hexanol and traces of glycerol by $^1$H NMR which corresponds to a 100.8% yield of 1-hexyl ozone esters. $^1$H NMR spectroscopy also indicated that the original triglyceride carboxylic acid sites were essentially completely transesterified with 1-hexanol to produce 1-hexyl ozone esters at these sites.

The approach and methodology as proposed in the present invention provides a solution towards producing an ester with improved yield. The characteristics and features of the present invention include, but are not limited to, reacting a substance having at least one carbon-to-carbon bond with ozone in the presence of a monoalcohol that azeotropes with water. In order to increase the yield of the final ester product, an additional refluxing step may be included, particularly before the second stage of ozonolysis.

The subject matter claimed herein is not limited to embodiments that solve any disadvantages or that operate only in environments such as those described above. Rather, this background is only provided to illustrate on exemplary technology area where some embodiments described herein may be practiced. Bibliographic references mentioned in the present specification are for convenience listed in the form of a list of references and added at the end of the examples. The whole content of such bibliographic references is herein incorporated by reference.

REFERENCES

1. WO2007027223
2. US 200902160040
3. WO2010078505
4. WO2010078498
5. WO2010078491
6. WO2010078493
7. U.S. Pat. No. 5,589,222

The invention claimed is:

1. A method for producing at least one ester, comprising:
   reacting at least one substance having at least one carbon-to-carbon double bond with ozone in the presence of at least one monoalcohol that azeotropes with water to produce at least one ester, wherein the ozone comprises at least one first mole of ozone per mole of carbon-to-carbon double bond of the at least one substance and at least one second mole of ozone per mole of carbon-to-carbon double bond of the at least one substance, the method further comprising:
   (a) refluxing and removing water by azeotropic distillation before adding the at least one second mole of ozone; or
   (b) refluxing and removing water by azeotropic distillation in the presence of at least one solvent that azeotropes with water before adding the at least one second mole of ozone.

2. The method according to claim 1, wherein the at least one solvent that azeotropes with water is selected from the group consisting of ethyl acetate, methyl acetate, ethyl propionate, methyl propionate, ethyl butyrate, methyl butyrate, ethyl isobutyrate, butyl acetate, butyl butyrate, isobutyl isobutyrate, and a mixture thereof.

3. The method according to claim 1, wherein the at least one monoalcohol that azeotropes with water comprises at least one monoalcohol with at least four carbon atoms.

4. The method according to claim 1, wherein the at least one monoalcohol that azeotropes with water comprises 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers thereof, 1-tetradecanol or isomers thereof, cetyl alcohol or isomers thereof, or stearyl alcohol or isomers thereof.

5. The method according to claim 1, wherein the at least one monoalcohol that azeotropes with water to form an azeotrope composition, and the azeotrope composition has a water content from a range of 4 to 90 percent water.

6. The method according to claim 1, wherein the at least one monoalcohol that azeotropes with water is 1-butanol or 1-hexanol.

7. The method according to claim 1, wherein the substance having at least one carbon-to-carbon double bond is reacted in the presence of an ozonolysis catalyst.

8. The method according to claim 1, wherein the substance having at least one carbon-to-carbon double bond comprises a vegetable oil, animal fat, or a mixture thereof.

9. The method according to claim 8, wherein the vegetable oil is selected from the group consisting of soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, and palm oil and the animal fat is selected from the group consisting of fish oil, tallow, duck fat, butter, and a mixture thereof.

10. The method according to claim 1, wherein the substance having at least one carbon-to-carbon double bond comprises a fatty acid.

11. The method according to claim 10, wherein the fatty acid is selected from the group consisting of: palm fatty acid distillates, palm kernel fatty acid distillates, fractionated palm fatty acid distillate, olein fatty acids, fractionated olein fatty acids, tallow fatty acids, fractionated tallow fatty acids, fractionated palm kernel fatty acid distillate, and fatty acids of the soybean oil, safflower oil, linseed oil, corn oil, sunflower oil, olive oil, canola oil, sesame oil, cottonseed oil, mustard oil, camelina oil, jatropha oil, nuts oil, peanut oil, coconut oil, rapeseed oil, Chinese tallow oil, tung oil, castor oil, wheat germ oil, soya oil, hemp oil, fish oil, algae oil, and a mixture thereof.

12. The method according to claim 1, wherein the substance having at least one carbon-to-carbon double bond comprises a fatty acid ester.

13. The method according to claim 1, wherein the at least one ester is at least one alkyl ester, and the at least one alkyl ester is transesterified to produce at least one ester alcohol in the presence of at least one primary polyol.

14. The method according to claim 13, wherein the at least one primary polyol is selected from the group consisting of glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, and combinations thereof.

15. A method for producing product ester polyols, comprising:
hydrolyzing at least one substance having at least one carbon-to-carbon double bond to produce a plurality of fatty acids;
reacting the plurality of fatty acids with ozone in the presence of a monoalcohol that azeotropes with water to produce a mixture of cleaved alkyl esters; and
converting the mixture of cleaved alkyl esters by transesterification with a primary polyol to a product ester polyol, wherein the ozone comprises at least one first mole of ozone per mole of carbon-to-carbon double bond of the at least one substance and at least one second mole of ozone per mole of carbon-to-carbon double bond of the at least one substance, the method further comprising:
(a) refluxing and removing water by azeotropic distillation before adding the at least one second mole of ozone; or
(b) refluxing and removing water by azeotropic distillation in the presence of at least one solvent that azeotropes with water before adding the at least one second mole of ozone.

16. The method for producing product ester polyols according to claim 15, further comprising:
performing fractionation by distillation of the mixture of cleaved alkyl esters before the transesterification of the mixture of cleaved alkyl esters.

17. The method for producing product ester polyols according to claim 15, wherein the mixture of cleaved alkyl esters are ozone esters, and the method further comprises:
performing fractionation by distillation of the mixture of ozone esters before the transesterification of the mixture of ozone esters.

18. The method for producing product ester polyols according to claim 15, wherein the at least one substance having at least one carbon-to-carbon double bond is a triglyceride.

19. The method for producing product ester polyols according to claim 18, further comprising:
performing fractionation by distillation of the mixture of cleaved alkyl esters before the transesterification.

20. The method according to claim 15, wherein the monoalcohol that azeotropes with water is 1-hexanol or 1-butanol.

21. A method for producing product ester polyols, comprising:
reacting at least one substance having at least one carbon-to-carbon double bond and a plurality of fatty acids with ozone and a monoalcohol that azeotropes with water to produce a mixture of cleaved alkyl esters; and
converting the mixture of cleaved alkyl esters by transesterification with a primary polyol to a product ester polyol, wherein the ozone comprises at least one first mole of ozone per mole of carbon-to-carbon double bond of the at least one substance and at least one second mole of ozone per mole of carbon-to-carbon double bond of the at least one substance, the method further comprising:
(a) refluxing and removing water by azeotropic distillation before adding the at least one second mole of ozone; or
(b) refluxing and removing water by azeotropic distillation in the presence of at least one solvent that azeotropes with water before adding the at least one second mole of ozone.

22. The method for producing product ester polyols according to claim 21, further comprising:
subjecting the mixture of cleaved alkyl esters to fractionation by distillation before the transesterification of the mixture of cleaved alkyl esters.

23. The method for producing product ester polyols according to claim 21, wherein the at least one substance having at least one carbon-to-carbon double bond is a triglyceride.

24. A method for producing at least one ester according to claim 1, comprising:
reacting at least one substance having at least one carbon-to-carbon double bond with at least one first mole of ozone per mole of carbon-to-carbon double bond of the at least one substance in the presence of at least one monoalcohol that azeotropes with water to form a reaction mixture;
refluxing the reaction mixture to remove water from the reaction mixture after the first mole of ozone was reacted;
reacting the reaction mixture with at least one second mole of ozone per mole of carbon-to-carbon double bond of the at least one substance; and
refluxing the reaction mixture after the at least one second mole of ozone was reacted.

25. The method according to claim 24, wherein the at least one substance having at least one carbon-to-carbon double bond is a fractionated palm oil fatty distillate, and the at least one monoalcohol that azeotropes with water is 1-butanol.

26. A method for producing at least one ester according to claim 1, comprising:
reacting at least one substance having at least one carbon-to-carbon double bond with at least one first mole of ozone per mole of carbon-to-carbon double bond of the at least one substance in the presence of at least one monoalcohol that azeotropes with water and at least one solvent that azeotropes with water to form a reaction mixture, the at least one substance having at least one carbon-to-carbon double bond is a partially fractionated olein;

refluxing the reaction mixture to remove water from the reaction mixture after the at least one first mole of ozone was reacted;

reacting the reaction mixture with at least one second mole of ozone per mole of carbon-to-carbon double bond of the at least one substance; and refluxing the reaction mixture after the at least one second mole of ozone was reacted.

27. The method according to claim 26, further comprising:

subjecting the at least one substance having at least one carbon-to-carbon double bond to purification to produce a mixture of fatty acids, wherein the at least one monoalcohol that azeotropes with water is 1-butanol, and the at least one solvent that azeotropes with water is butyl acetate.

28. The method for producing at least one ester according to claim 26, wherein the at least one substance having at least one carbon-to-carbon double bond is methyl olein, the at least one monoalcohol that azeotropes with water is 1-hexanol, and the at least one ester includes 1-hexyl ozone esters.

* * * * *